United States Patent [19]

Noda

[11] Patent Number: 4,653,577

[45] Date of Patent: Mar. 31, 1987

[54] UNITARY HEAT EXCHANGER AND DEBUBBLER FOR A LIQUID

[75] Inventor: Wayne A. Noda, Mission Viejo, Calif.

[73] Assignee: Shiley, Inc., Irvine, Calif.

[21] Appl. No.: 821,672

[22] Filed: Jan. 23, 1986

[51] Int. Cl.$^4$ ............................................. F16F 1/34
[52] U.S. Cl. .................................... 165/71; 165/103; 165/917; 165/156; 422/46; 422/47
[58] Field of Search ............... 165/71, 103, 917; 422/46, 47

[56] References Cited

U.S. PATENT DOCUMENTS

| | | | |
|---|---|---|---|
| 3,825,060 | 7/1974 | Heller et al. | 165/71 X |
| 4,065,264 | 12/1977 | Lewin | 422/46 |
| 4,282,180 | 8/1981 | Raible | 422/46 |
| 4,559,999 | 12/1985 | Servas et al. | 422/46 X |
| 4,568,330 | 2/1986 | Kujawski et al. | 604/53 |

Primary Examiner—Albert W. Davis, Jr.
Assistant Examiner—Richard R. Cole
Attorney, Agent, or Firm—C. J. Knuth; L. C. Akers

[57] ABSTRACT

A compact unitary heat exchanger and debubbler for a liquid includes an elongated heat exchange element having an inverted V-shape and a vertically-extending debubbling chamber located between the legs of the inverted V. The heat exchange element is made up of an inner tube surrounded by an outer tube, so that a heat exchange fluid such as water flowing within the inner tube exchanges heat with a treated liquid flowing within a space defined between the inner and outer tubes. After passing through the heat exchange element the treated liquid passes through the debubbling chamber and then through the device outlet. A bypass passageway in the vicinity of the treated liquid inlet to the device connects the debubbling chamber with the space between the inner and outer tubes of the heat exchange element. A valve movable into open and closed positions is provided in this bypass passageway. With this valve in the open position the device can be primed through the treated liquid inlet prior to use with the risk of gas bubble formation and entrapment during priming essentially eliminated. This is a very important feature when the device is used to treat liquids being administered to the human circulatory system. The device may also include a filter in the debubbling chamber positioned in series with the treated liquid outlet.

4 Claims, 5 Drawing Figures

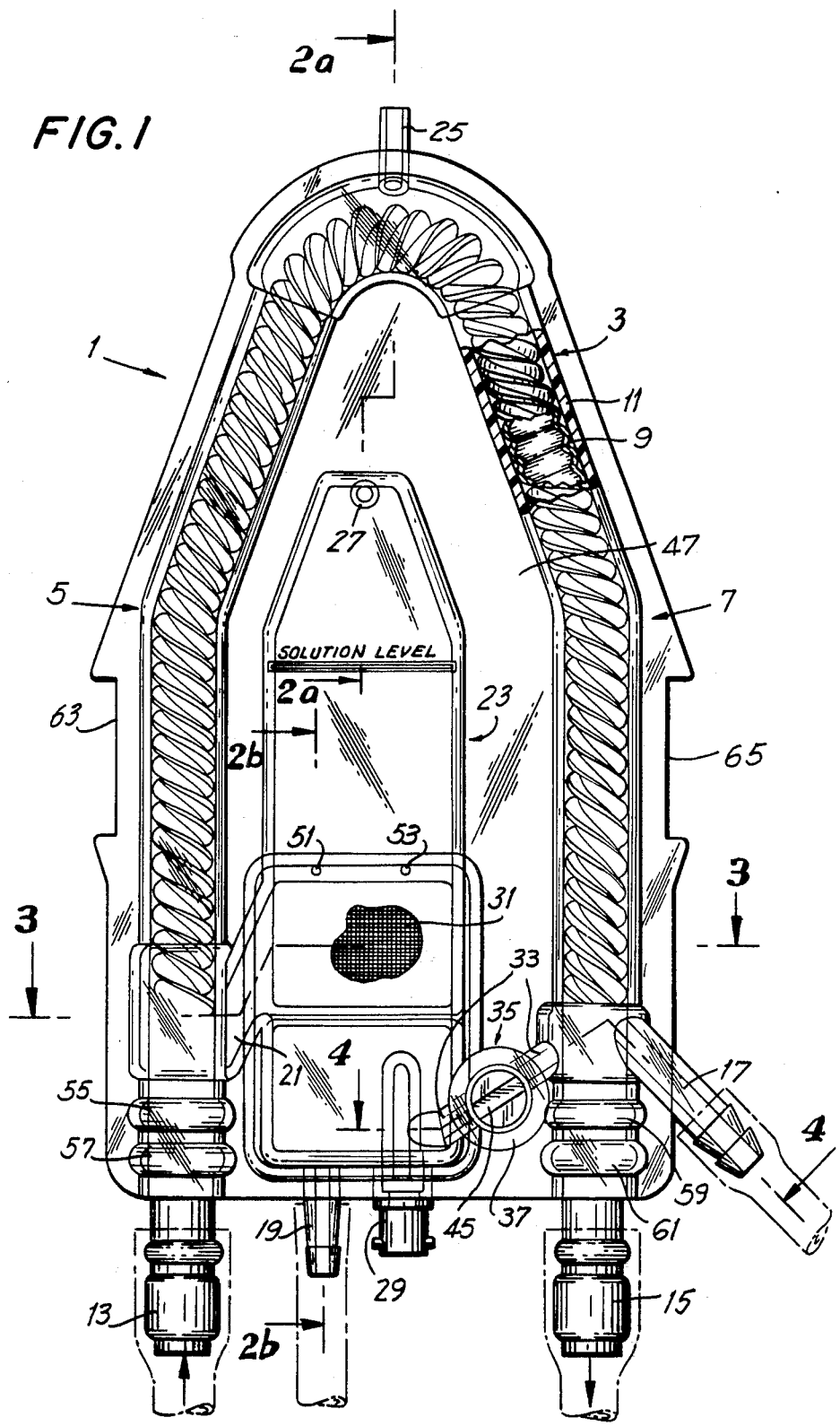

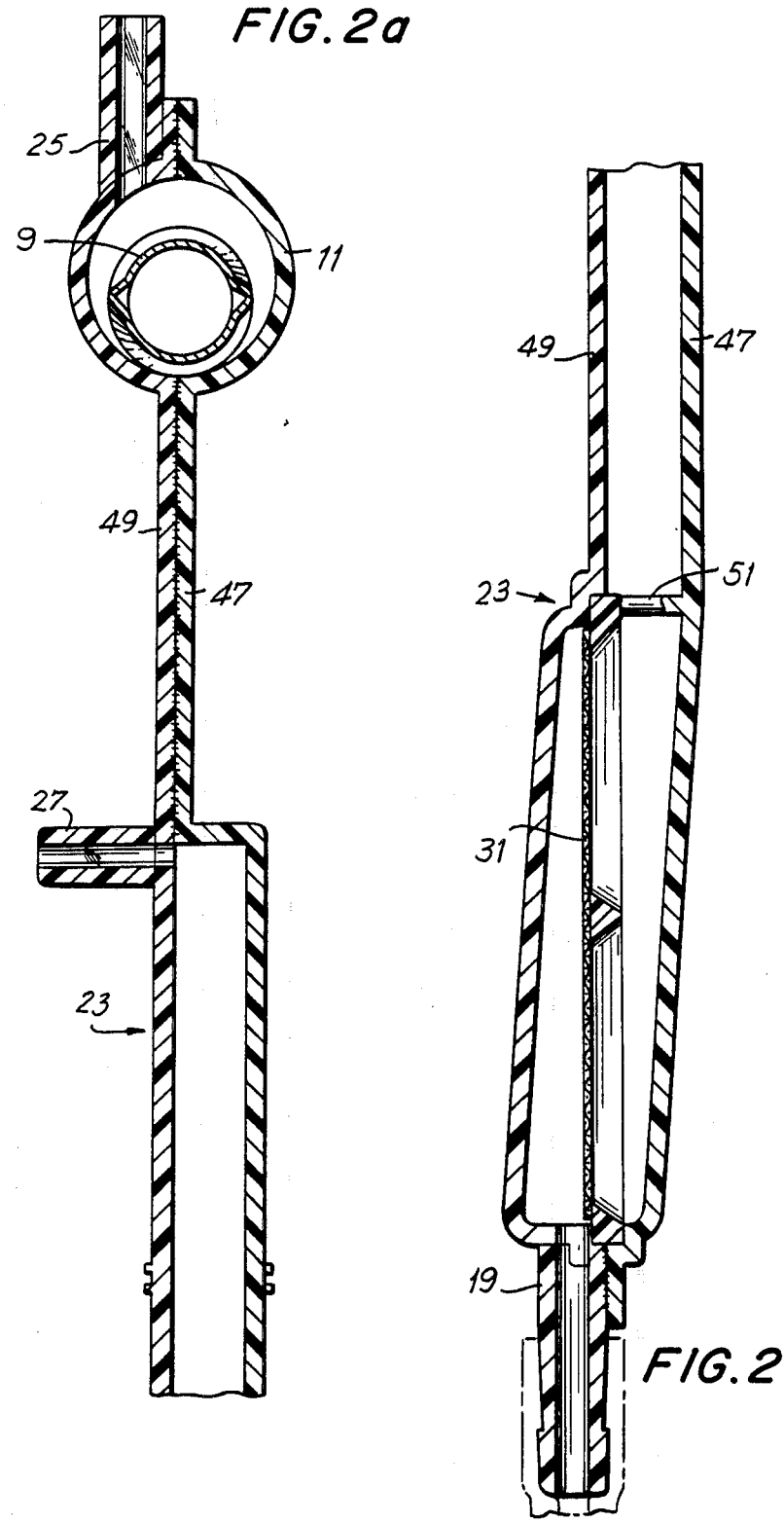

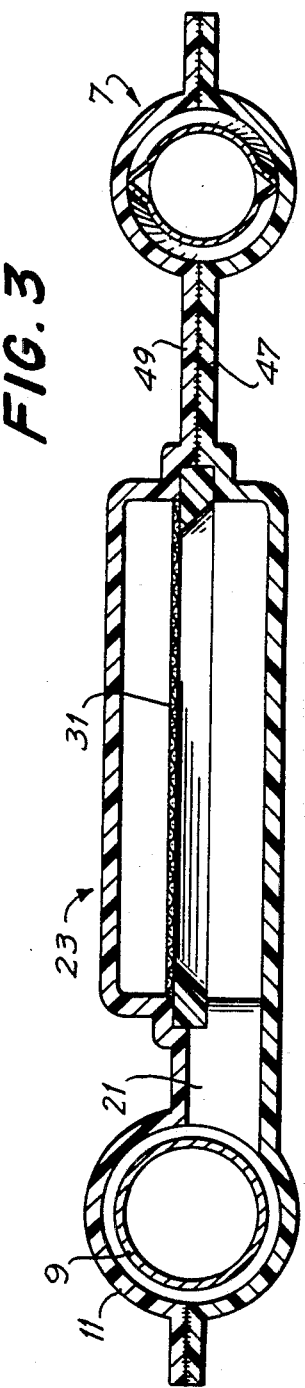
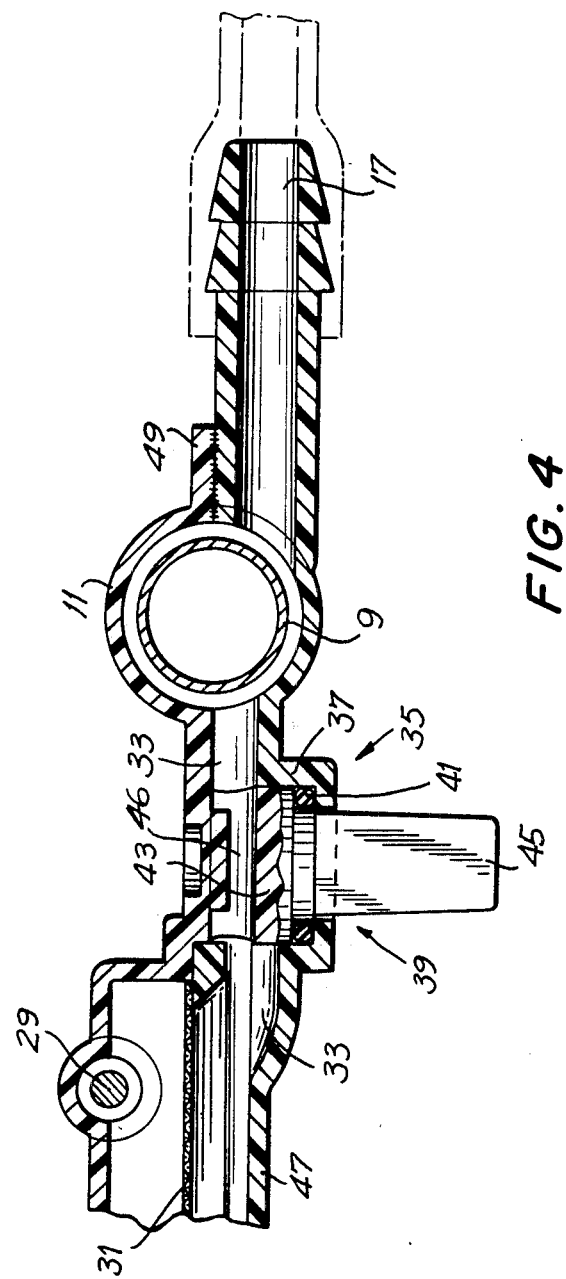

UNITARY HEAT EXCHANGER AND DEBUBBLER FOR A LIQUID

BACKGROUND OF THE INVENTION

The present invention relates to the field of treatment of liquids, especially liquids being administered to the circulatory system of a human patient.

In many situations it is desired to administer a liquid into the circulatory system of a patient before, during or after a surgical operation. Thus, it is known to administer a cardioplegia solution to the coronary arteries in order to arrest the heart so that open heart surgery can be performed. The administered cardioplegia solution should be cold (e.g. from about 10° to 15° C.) so that it also serves to cool, and thereby reduce the metabolic requirements of, the patient's heart tissue. The cardioplegia solution may be beneficially administered in admixture with the patient's whole blood in order to supply oxygen and nutrients to the heart tissue along with the cardioplegia solution.

It is known to include a heat exchanger in the cardioplegia solution (or blood/cardioplegia solution) delivery line for cooling purposes. However, the known heat exchangers used for this purpose generally suffer from one or more of the disadvantages of a non-compact size and shape, an undesirably large priming volume, an undesirably low heat exchange capacity and/or efficiency, an inadequate capability to remove any gas bubbles present in the treated liquid inlet stream, an excessive treated liquid pressure drop across the device, a tendency to significantly damage blood constituents in the treated liquid, or a propensity to form gas bubbles in the treated liquid flow regions during priming of the heat exchanger (caused for example by splashing of priming liquid within unfilled treated liquid flow channels) that might be carried through the device outlet to the patient. It is of course vitally important to remove any gas bubbles in the treated liquid inlet stream as well as to avoid the formation within the device of gas bubbles in the priming liquid during priming and in the treated liquid during subsequent operation because of the potentially disastrous consequences of introducing gas bubbles into a patient's circulatory system.

SUMMARY OF THE INVENTION

It is an object of the present invention to provide a heat exchanger for a liquid, for example a cardioplegia solution or a blood/cardioplegia solution mixture, having a compact size and shape, a low priming volume and a high heat exchange capacity and efficiency, in which removal of any gas bubbles in the treated liquid inlet stream is assured, the risk of formation of gas bubbles in the priming liquid during priming is essentially avoided, treated liquid pressure drops across the device are not excessive and no significant damage to blood constituents (if present) in the treated liquid occurs.

It is a further object of the invention to provide a heat exchanger having the characteristics described in the preceding paragraph that is inexpensive, disposable after a single use and light in weight.

These and other objects may be achieved with a novel unitary heat exchanger and debubbler for a liquid comprising: an elongated heat exchange element comprising an inner tube for conduction of a heat exchange fluid and an outer tube surrounding the inner tube, with a space being defined between the inner and outer tubes for conduction of a treated liquid in heat exchanging relationship with the heat exchange fluid, said element generally having an inverted V-shape with two legs extending from a highest point at the junction of said two legs; a heat exchange fluid inlet in communication with one end of the inner tube; a heat exchange fluid outlet in communication with the other end of the inner tube; a treated liquid inlet at one end of the heat exchange element in communication with the space between the inner and outer tubes; a first port at said highest point of the heat exchange element in communication with the space between the inner and outer tubes; an elongated vertically-extending debubbling chamber located between the legs of the heat exchange element; a second port adjacent the top of, and in communication with, the debubbling chamber; a treated liquid passageway at the end of the heat exchange element opposed to the treated liquid inlet connecting the debubbling chamber with the space between the inner and outer tubes; a treated liquid outlet at the bottom of the debubbling chamber; a bypass passageway in the vicinity of said treated liquid inlet connecting the debubbling chamber with the space between the inner and outer tubes; and a priming valve in said bypass passageway capable of being moved into open and closed positions. Because of its inverted V-shaped configuration, a heat exchange element having a substantial length, thereby affording a substantial heat exchange capacity, can be utilized in the device of the invention without sacrificing the desired compact size and shape of the device. The debubbling chamber conveniently fits within the unused space between the legs of the inverted V and thus adds a highly important additional function (i.e. gas bubble removal from the treated liquid) with negligible contribution to the overall dimensions of the device.

Without inclusion of the aforementioned bypass passageway in the vicinity of the treated liquid inlet, it would be necessary to prime the two legs of the heat exchange element sequentially. After one leg was filled from bottom to top the priming liquid would spill over into the other leg and tend to splash in that leg while filling it. This splashing action of the priming liquid would in turn tend to generate gas bubbles that might be carried to the patient. This potential problem is not realized, however, in the device of the present invention. When the novel device is primed through the treated liquid inlet with the aforementioned priming valve in the open position, the two legs of the heat exchange element and the debubbling chamber between these legs are all filled simultaneously with the priming liquid from bottom to top. After completion of priming the priming valve is placed into the closed position to begin treatment of, for example, a blood/cardioplegia solution mixture.

Preferably, the device of the invention comprises additionally a filter (for example a screen filter) disposed in the debubbling chamber in such a manner that the port adjacent the top of the debubbling chamber and the aforementioned treated liquid passageway are on its upstream side and all of the treated liquid flowing to the treated liquid outlet must first pass through the filter. This filter provides a barrier against the passage of particulate matter or gas bubbles to the patient.

It is also preferred, in order to particularly enhance the heat exchange capacity and efficiency of the device, that the inner tube of the elongated heat exchange element be helically-ribbed on its exterior along its length, that the inner wall of the outer tube of the heat exchange element be smooth, and that said inner and outer tubes be in a close fit over a major portion of the length of the heat exchange element so that at least a major portion of the treated liquid flowing through the heat exchange element passes through the helically-shaped passage or passages defined by the outer surface of the helically-ribbed inner tube

DETAILED DESCRIPTION OF THE INVENTION

The invention will be described in detail with reference to a preferred embodiment thereof, which is a disposable unitary heat exchanger, debubbler and filter particularly suitable for use in treating a liquid being administered into the circulatory system of a human patient. Reference to this embodiment does not limit the scope of the invention, which is limited only by the scope of the claims. In the drawings:

FIG. 1 is a front elevational view of a disposable unitary heat exchanger, debubbler and filter of the invention, with the priming valve shown in the open position;

FIGS. 2a and 2b are sectional views taken along lines 2a—2a and 2b—2b respectively in FIG. 1;

FIG. 3 is a sectional view taken along line 3—3 in FIG. 1; and

FIG. 4 is a sectional view taken along line 4—4 in FIG. 1.

A disposable unitary heat exchanger, debubbler and filter 1 of the invention is shown in FIGS. 1 to 4. This device 1 is intended to be used in the vertically-extending orientation shown in FIG. 1. Device 1 includes an elongated heat exchange element 3 having the approximate configuration of an inverted V, with the two legs 5 and 7 of element 3 joined at the highest point of the inverted V. As is shown in FIG. 1, both of the legs 5 and 7 are bent so that the lower segments of the two legs are substantially parallel. The heat exchange element 3 is formed by an inner tube 9 surrounded by an outer tube 11. Device 1 also includes a heat exchange fluid inlet 13 and a heat exchange fluid outlet 15 in communication with opposed ends of inner tube 9. The heat exchange fluid (e.g. cooling water) flows sequentially through inlet 13, inner tube 9 and outlet 15. The device 1 further includes an inlet 17 at the end of leg 7 and an outlet 19 for the liquid being treated in the device (referred to herein as the "treated liquid"), which may be for example a mixture of the patient's blood and a cardioplegia solution. While flowing through inner tube 9 the heat exchange fluid is in countercurrent heat exchange relationship with the treated liquid, which flows through the space defined between inner and outer tubes 9 and 11. The treated liquid flows sequentially through inlet 17 (which is in communication with the interior of outer tube 11), the space between inner and outer tubes 9 and 11, passageway 21 at the end of leg 5, debubbling chamber 23 and outlet 19 at the bottom of chamber 23. A port 25 in communication with the space between inner and outer tubes 9 and 11 is provided at the highest point of the heat exchange element 3, for purposes to be described below.

In the embodiment shown in FIGS. 1 to 4, the inner tube 9 is helically-ribbed on its exterior along its length and outer tube 11 has a smooth inner wall. Except at the two ends of legs 5 and 7, in the vicinity of passageway 21 and inlet 17, and at the highest point of heat exchange element 3, in the vicinity of port 25, where outer tube 11 has a somewhat enlarged inner diameter, inner tube 9 and outer tube 11 are in a close fit so that a major portion (preferably substantially all) of the treated liquid flowing through element 3 is confined to follow the helically-shaped passages defined by the outer surface of the inner tube 9. In the embodiment of FIGS. 1 to 4, four continuous hollow ribs are provided on the outer surface of inner tube 9 which in turn create four continuous helical passages for the treated liquid. Outer tube 11 has an enlarged inner diameter in the vicinity of passageway 21 and inlet 17 to form a pair of manifold regions providing equal distribution of treated liquid flow around the inner tube 9, and thus equal flow distribution through the four helical passages.

An elongated vertically-extending debubbling chamber 23 for the treated liquid is located between the legs 5 and 7 of the heat exchange element 3. A port 27 in communication with the interior of chamber 23 is provided adjacent the top of chamber 23, for purposes to be described below. The treated liquid outlet 19 and the passageway 21 leading from the end of leg 5 are also, of course, in communication with the interior of the debubbling chamber 23. Passageway 21 is oriented in an upward/inward fashion (see FIG. 1) so that any gas bubbles in the treated liquid stream therein are directed upwardly towards port 27. A temperature probe 29 extending into the debubbling chamber 23 is provided to enable the measurement of the treated liquid temperature adjacent the outlet 19. The debubbling chamber 23 is of sufficient volume to allow for a complete separation by bouyancy of any gas bubbles in the treated liquid during the residence time of the treated liquid in the chamber 23 within a wide range of expected throughput rates. As an additional safety feature, a vertically-extending filter 31 is provided within the debubbling chamber 23 downstream of passageway 21 and port 27 and upstream of outlet 19. The filter 31 should have a sufficiently low effective pore size to provide a positive barrier against gas bubbles or undesired solid particulate matter that might be present in the treated liquid. As one example, filter 31 may comprise a woven polyester screen having a pore size of about 105 microns supported by a plastic frame.

An important feature of the device 1 shown in FIGS. 1 to 4 is the inclusion of a bypass passageway 33 connecting the debubbling chamber 23 with the space between inner and outer tubes 9 and 11 at the end of leg 7 in the vicinity of inlet 17. A rotary priming valve 35 capable of being moved into open and closed positions is located within the passageway 33. Priming valve 35 is closed during the treatment of a treated liquid in device 1 but is opened for priming of the device, as will be explained below. Valve 35 comprises a valve housing 37, a valve element 39 and a silicone rubber compression O-ring 41. Valve element 39 includes a generally cylindrical valve body 43 and a relatively flat valve stem 45. The priming valve 35 is opened by rotating the valve body 43 with the valve stem 45 until a straight diametrical channel 46 formed in the back surface of valve body 43 is brought into alignment with the portions of bypass passageway 33 on either side of the priming valve 35. Conventional stop means (not shown in the figures) are included to limit the rotation of valve body 43 between an open position and a closed position about 125° clockwise thereto (as viewed in the front view of FIG. 1). The bypass passageway 33 communicates with a portion of debubbling chamber 23 that is upstream of filter 31, so that any treated liquid inadvertently passing through bypass passageway 33 (e.g. in the case of an accidental opening of valve 35) must first pass through filter 31 before going to outlet 19.

All of the structural features of the device 1 shown in FIGS. 1 to 4, except for the inner tube 9, filter 31, temperature probe 29, valve element 39 and O-ring 41, are formed by a front panel 47 and a rear panel 49 which are adapted to be bonded together in the construction of the device. Treated liquid inlet 17 is in one-piece construction with front panel 47, while treated liquid outlet 19 and ports 25 and 27, and the port holding probe 29, are in one-piece construction with rear panel 49. Suitably configured relieved patterns on one or both of the panels 47 and 49 structurally define the outer tube 11, passageways 21 and 33, debubbling chamber 23 and valve housing 37. Panels 47 and 49 are preferably made from a transparent plastic material, most preferably a thermoplastic such as a polycarbonate. Valve element 39 is preferably made from an inert opaque plastic material, most preferably a thermoplastic such as an acetal polymer. Manufacture of panels 47 and 49 and element 39 by injection molding is preferred for reasons of cost. Inner tube 9 is preferably made of aluminum anodized on its outer surface in a conventional manner for blood compatibility.

In the assembly of device 1, the frame of filter 31 is bonded to rear panel 49 by solvent welding. Two pins 51 and 53 in one-piece construction with front panel 47 insure that the upper portion of the filter remains properly spaced from the front panel 47. Panels 47 and 49 are bonded together, with inner tube 9, O-ring 41 and valve element 39 in place, by means of solvent welding, preferably using a mixture of dichloromethane and dichloroethane when panels 47 and 49 are made of a polycarbonate. Inner and outer tubes 9 and 11 are sealed together below inlet 17 and passageway 21 with a suitable polyurethane applied through small holes (not shown in the figures) in ribs 55, 57, 59 and 61 structurally defined by panels 47 and 49. Temperature probe 29 is bonded in place to panel 49 by solvent welding.

In operation to treat a blood/cardioplegia solution mixture being administered to a patient, a line of tubing extending downstream from a Y-connector is connected to the treated liquid inlet 17. Two lines of tubing extend upstream from this Y-connector through a single peristaltic pump head and then to two separate reservoirs holding patient's blood and cardioplegia solution. Another line of tubing is connected to the treated liquid outlet 19. When heart arrest is being performed as an adjunct to open heart surgery, the latter line of tubing is connected to a needle inserted in a conventional manner into the aorta, with the aorta being clamped downstream of the insertion point to force the treated liquid into the coronary arteries. When aortic valve replacement is being performed, the line of tubing extending from outlet 19 is connected to another Y-connector, and two lines of tubing extend downstream from this Y-connector to a pair of coronary perfusion cannulae, each of which cannulae is inserted into a different coronary artery. Device 1 is held in use in the vertical orientation shown in FIG. 1, preferably in a holder provided with spring-loaded plungers adapted to fit securely within notches 63 and 65.

Regardless of the surgical procedure being performed, device 1 must be properly primed with a priming liquid (typically patient's blood or normal saline) prior to its treatment of the treated liquid. A conventional stopcock (not shown in the figures) is connected to each of ports 25 and 27 and manipulated into the open position. Preferably, a conventional pressure gage is connected between port 27 and its stopcock for the monitoring of perfusion pressure. The priming liquid is introduced through inlet 17 with priming valve 35 in the open position. Because of the unique structural features of the present invention, legs 5 and 7 of the heat exchange element 3 and the debubbling chamber 23 are simultaneously and gently filled with the priming liquid in a bottom-to-top fashion. Consequently, vigorous splashing of the priming liquid within device 1 that might lead to the formation of potentially dangerous gas bubbles within the priming liquid is avoided. When the level of priming liquid in debubbling chamber 23 reaches the "SOLUTION LEVEL" line engraved in the front surface of panel 47 (see FIG. 1), the stopcock associated with port 27 is closed. The stopcock associated with port 25 is closed only after priming liquid has begun to bleed through that stopcock.

Once priming has been completed, valve element 39 is rotated to place priming valve 35 in the closed position, and the treated liquid is introduced into the inlet 17. A heat exchange fluid (e.g. cooling water) is circulated through the inner tube 9, preferably in a countercurrent relationship to the treated liquid. Any substantial accumulation of gas in the top of the debubbling chamber 23 can be readily detected by a lowering of the liquid level therein below the "SOLUTION LEVEL" line. This accumulated gas can be readily released during treated liquid delivery by briefly opening the stopcock associated with port 27 until the correct liquid level in the debubbling chamber 23 is restored.

It thus can be seen that the handling, setting up and operation of device 1 by surgical personnel is a very simple and efficient matter.

What is claimed is:

1. A unitary heat exchanger and debubbler for a liquid comprising
    an elongated heat exchange element generally having an inverted V-shape with two legs extending from a highest point at the junction of said two legs and comprising an inner tube for conduction of a heat exchange fluid and an outer tube surrounding the inner tube, with a space being defined between said inner and outer tubes for conduction of a treated liquid in heat exchanging relationship with the heat exchange fluid;
    a heat exchange fluid inlet in communication with one end of said inner tube;
    a heat exchange fluid outlet in communication with the other end of said inner tube;
    a treated liquid inlet at one end of said heat exchange element in communication with the space between said inner and outer tubes;
    a first port at said highest point of said heat exchange element in communication with the space between said inner and outer tubes;
    an elongated vertically-extending debubbling chamber located between said legs of the heat exchange element;
    a second port adjacent the top of, and in communication with, the debubbling chamber;
    a treated liquid passageway at the end of said heat exchange element opposed to the treated liquid inlet connecting the debubbling chamber with the space between said inner and outer tubes;
    a treated liquid outlet at the bottom of the debubbling chamber;

a bypass passageway in the vicinity of said treated liquid inlet connecting the debubbling chamber with the space between said inner and outer tubes; and a priming valve in said bypass passageway capable of being moved into open and closed positions.

2. A unitary heat exchanger and debubbler of claim 1 wherein said inner tube is helically-ribbed on its exterior along its length and said outer tube has a smooth inner wall, with said inner and outer tubes being in a close fit so that at least a major portion of the treated liquid flowing through the heat exchange element passes through the helically-shaped passage(s) defined by the outer surface of the helically-ribbed inner tube.

3. A unitary heat exchanger and debubbler of claim 2 comprising additionally a filter disposed in said debubbling chamber in such a manner that said treated liquid passageway and said second port are on the upstream side of the filter and all of the treated liquid flowing through the debubbling chamber to the treated liquid outlet must first pass through said filter.

4. A unitary heat exchanger and debubbler of claim 1 comprising additionally a filter disposed in said debubbling chamber in such a manner that said treated liquid passageway and said second port are on the upstream side of the filter and all of the treated liquid flowing through the debubbling chamber to the treated liquid outlet must first pass through said filter.

* * * * *